US006518288B2

(12) United States Patent
Lemmens et al.

(10) Patent No.: US 6,518,288 B2
(45) Date of Patent: Feb. 11, 2003

(54) AMLODIPINE FUMARATE

(75) Inventors: Jacobus M. Lemmens, Mook (NL); Theodorus H. A. Peters, Arnhem (NL); Franciscus B. G. Benneker, Rheden (NL); Frantisek Picha, Brno (CZ)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 09/938,820

(22) Filed: Aug. 27, 2001

(65) Prior Publication Data

US 2002/0123519 A1 Sep. 5, 2002

Related U.S. Application Data

(63) Continuation-in-part of application No. 09/809,350, filed on Mar. 16, 2001, now abandoned.
(60) Provisional application No. 60/258,604, filed on Dec. 29, 2000.

(51) Int. Cl.$^7$ ...................... C07D 211/86; A61K 31/455
(52) U.S. Cl. ........................................ 514/356; 546/321
(58) Field of Search ........................... 546/321; 514/356

(56) References Cited

U.S. PATENT DOCUMENTS

| | | | | |
|---|---|---|---|---|
| 4,572,909 A | * | 2/1986 | Campbell et al. | 514/536 |
| 4,870,091 A | * | 9/1989 | Peglion et al. | 514/356 |
| 4,879,303 A | | 11/1989 | Davison et al. | |
| 4,983,740 A | | 1/1991 | Peglion et al. | |
| 5,155,120 A | | 10/1992 | Lazar et al. | |
| 5,389,654 A | | 2/1995 | Furlan et al. | |
| 5,438,145 A | | 8/1995 | Furlan et al. | |
| 6,046,337 A | | 4/2000 | Bozsing et al. | |

FOREIGN PATENT DOCUMENTS

| | | |
|---|---|---|
| EP | 0 089 167 B1 | 10/1986 |
| EP | 0 244 944 | 1/1990 |
| EP | 0 290 211 B1 | 9/1991 |
| EP | 0 534 520 B1 | 3/1997 |
| EP | 0 902 016 A1 | 3/1999 |
| EP | 0 963 980 A2 | 12/1999 |
| WO | 99/25688 | 5/1999 |
| WO | 99/52873 | 10/1999 |
| WO | 00/24714 | 5/2000 |
| WO | 00/35873 | 6/2000 |
| WO | 00/35910 | 6/2000 |

OTHER PUBLICATIONS

Alker et al., "Long–acting dihydropyridine calcium antagonists. 9. Structure activity relationships around amlodipine", Eur J Med Chem (1991) 26, 907–913.
Amlodipine Besylate Monograph, Pharmeuropa vol. 10, No. 2, 197–198, Jun. 1998.
Faulkner et al, "Absorption of Amlodipine Unaffected by Food", Arzneim Forsch/Drug Res. 39 (11), No. 7, (1989).
McDaid and Deasy, "Formulation development of a transdermal drug delivery system for amlodipine base", International Journal of Pharmaceutics 133 (1996) 71–83.
Arrowsmith et al., "Long–Acting Dihydropyridine Calcium Antagonists. 1. 2–Alkoxymethyl Derivatives Incorporating Basic Substituents", J. Med. Chem. American Chemical Society, 1986, 29, 1696–1702.
FDA FOIA Material on Amlodipine Besylate, NDA No. 19–787, "Review of an Original NDA", Oct. 10, 1990.

* cited by examiner

*Primary Examiner*—Jane Fan
(74) *Attorney, Agent, or Firm*—Fleshner & Kim, LLP

(57) ABSTRACT

Amlodipine fumarate salt compounds are useful as calcium channel blockers and in treating or preventing angina or hypertension. The fumarate salts avoid the formation of certain potential impurities that have been found to be associated with amlodipine maleate.

13 Claims, No Drawings

AMLODIPINE FUMARATE

This application is a continuation-in-part application under 35 U.S.C. §120 of prior U.S. application Ser. No. 09/809,350, filed Mar. 16, 2001, now abandoned the entire contents of which are incorporated herein by reference. Further this application claims the benefit of priority under 35 U.S.C. §119(e) from provisional patent application Ser. No. 60/258,604, filed Dec. 29, 2000, the entire contents of which are incorporated herein by reference.

BACKGROUND OF THE INVENTION

1. Field of the Invention

The present invention relates to a novel compound, to processes for preparing it and to its use in treating medical disorders. In particular the present invention relates to novel acid addition salts of amlodipine.

2. Description of the Related Arts

Calcium channel blockers (calcium antagonists) are useful in treating cardiac conditions including angina and/or hypertension. Dicarboxylate-dihydropyridine derivatives are generally known to possess calcium channel blocking activity. For example, EP 089 167 and corresponding U.S. Pat. No. 4,572,909 disclose a class of 2-amino group-3,5-dicarboxylate dihydropyridine derivatives as being useful calcium channel blockers. These patents identify that one of the most preferred compounds is 2-[(2-aminoethoxy)methyl]-4-(2-chlorophenyl)-3-ethoxycarbonyl-5-methoxycarbonyl-6-methyl-1,4-dihydropyridine. This compound, which is now commonly known as amlodipine, has the following formula:

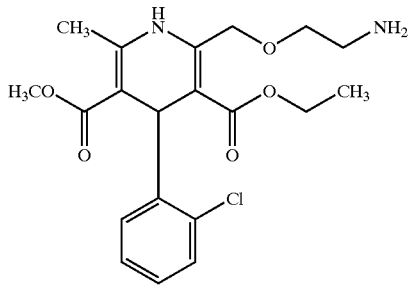

Amlodipine exhibits good bioavailability and has a long half-life in the body. While a variety of acid addition salts are mentioned in these patents as being potentially suitable, including fumarates, the maleate salt is identified as the most preferred acid addition salt. However, the commercial product of amlodipine (NORVASC by Pfizer) uses amlodipine besylate (benzene sulfonate) and not amlodipine maleate. Indeed, subsequent patents EP 244 944 and corresponding U.S. Pat. No. 4,879,303 indicate that the besylate salt provides certain advantages over the known salts including good formulating properties. Apparently, amlodipine maleate suffered from tabletting and stability problems so as to cause a switch during development to the besylate salt. (See "Review of Original NDA" for NDA# 19-787 of Oct. 10, 1990, obtainable from FDA under Freedom of Information Act). The stability and tabletting issues/causes are not publicly disclosed in the information available from the FDA.

SUMMARY OF THE INVENTION

The present invention relates to fumarate salts of amlodipine. In particular, one aspect of the invention relates to an acid addition salt of amlodipine with fumaric acid. Another aspect of the invention relates to amlodipine fumarate in a crystalline state. A preferred form of amlodipine fumarate is amlodipine hemifumarate.

The invention also relates to a process, which comprises contacting amlodipine free base or a salt thereof with fumaric acid or its ammonium salt in the presence of a solvent to form amlodipine fumarate.

Further aspects of the invention include a method for treating or preventing angina or hypertension which comprises administering to a patient in need thereof an effective amount of amlodipine fumarate as well as to a pharmaceutical composition for use in the treatment and/or prevention of angina or hypertension that comprises an effective amount of amlodipine fumarate together with a pharmaceutically acceptable excipient.

DETAILED DESCRIPTION OF THE INVENTION

This invention relates to a novel salt of amlodipine that does not comprise problems associated with the maleate salt and is a suitable equivalent to the besylate salt. According to the present invention there is provided an acid addition salt of amlodipine with fumaric acid, i.e. amlodipine fumarate.

Fumaric acid, unlike maleic acid, exists in a trans configuration. It has now been discovered that a problem with the formation and/or stability of amlodipine maleate is the potential for the amine nitrogen of amlodipine to react with the double bond of the maleic acid to form an amlodipine aspartate of the following formula.

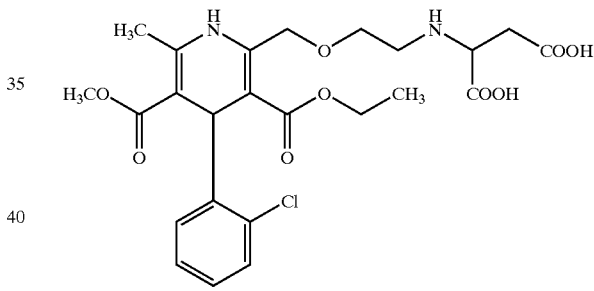

This reaction is a Michael-type addition. The present invention avoids the formation of amlodipine aspartate by selecting a different salt anion. In particular, although both maleic acid and fumaric acid contain a carbon double bond, the Michael-type addition is prevented from occurring with fumaric acid because of this acid's trans configuration. Accordingly an aspartate derivative can not be formed with fumaric acid and this particular impurity/stability issue now known to be associated with amlodipine is avoided.

Amlodipine fumarate as used herein means any acid addition salt formed by reacting/combining fumaric acid with amlodipine; e.g. any salt comprised of amlodipine cations and fumaric acid anions. For instance, solid as well as dissolved forms are included as are crystalline and amorphous forms. Further, the ratio of amlodipine to fumaric acid is not required to be 1:1, although such is included, in order to be an amlodipine fumarate compound. For example, a preferred amlodipine fumarate has a ratio of 2:1, which corresponds to a hemifumarate. These and other specific ratios of amlodipine to fumaric acid are all embraced by the single generic term "amlodipine fumarate." The crystal forms can be anhydrates, hydrates, solvates, etc. Further, it should be understood that the compound can exist as one of two enantiomers due to the presence of a chiral center on the 1,4-dihydropyridine ring. The forms may be separated e.g., by crystallisation or chromatography of the amlodipine free base or a salt thereof with an optically active acid, and converted to the corresponding fumarate salt. The individual enantiomers as well as mixtures thereof are likewise all embraced by the singular expression "amlodipine fumarate."

Amlodipine fumarate can be prepared by contacting amlodipine (as the free base) or its acid addition salt other than the fumarate, with fumaric acid or its ammonium salt in a suitable solvent, preferably with both the fumaric acid and amlodipine being fully dissolved therein. Generally the amlodipine fumarate is precipitated out of the solution or reaction mixture. The precipitation may be spontaneous depending upon the solvent used and the conditions. Alternatively, the precipitation can be induced by reducing the temperature of the solvent, especially if the initial temperature at contact is elevated. The precipitation may also be facilitated by reducing the volume of the solution or by adding a contrasolvent, i.e. a liquid miscible with the solvent in which the amlodipine fumarate is less soluble.

The amlodipine or salt thereof to be used in making the present invention can be obtained by methods well known in the art including those described in the above-mentioned patents as well as in U.S. Pat. No. 4,572,909. Another useful synthesis scheme for making amlodipine or salts thereof in good yields and purity via a phthalimidoamlodipine intermediate is also described in commonly-owned provisional application serial No. 60/258,613 filed Dec. 29, 2000, the entire contents of which are incorporated herein by reference, and in commonly-owned U.S. patent application Ser. No. 09/809,351, filed on Mar. 16, 2001 and entitled "Process for Making Amlodipine, Derivatives Thereof, and Precursors Therefor," the entire contents of which are incorporated herein by reference. Fumaric acid and ammonium salts thereof are well known per se and are readily available to the worker skilled in the art.

Solvents useful for carrying out the salt reaction include water, alcohol such as methanol or ethanol, ketone such as acetone or methyl isobutyl ketone, ester such as ethylacetate, ether such as diethylether or tetrahydrofuran, nitrile such as acetonitrile, dipolar aprotic solvents such as dimethylsulfoxide or dimethylformamide, hydrocarbons such as hexane or toluene and mixtures thereof. Preferred solvents are those wherein the reactants are more soluble than the amlodipine fumarate product. In this way, the salt forming reaction is accompanied by spontaneous precipitation of the produced fumarate salt out of the solution. Examples are alcohols such as ethanol and isopropanol, esters such as ethyl acetate, and hydrocarbons such as toluene.

The precipitated fumarate salt may be isolated in a solid state by conventional methods such as filtration or centrifugation, optionally followed by washing and/or drying and may be purified by crystallization, for example at elevated temperature in an appropriate solvent, for example water, an alcohol such as methanol, or a ketone such as acetone. The above described methods allow for the production of an amlodipine fumarate compound in a crystalline state.

Amlodipine fumarate is preferably formed as a salt having a 2:1 molar ratio between amlodipine and fumaric acid (=amlodipine (2:1) fumarate or amlodipine hemifumarate) as such salt is insoluble or only sparingly soluble in water and most commonly used organic solvents. Amlodipine hemifumarate may be formed even when an excess of amlodipine or an excess of fumaric acid is used in the salt formation. Because of its limited water solubility, amlodipine hemifumarate is a preferred compound for certain embodiments of the present invention, especially for slow or extended release pharmaceutical compositions. By having a lower water solubility, the release profile of amlodipine in the body can be more easily moderated and extended. By using this salt as an active ingredient in tablets or capsules, other means for enhancing slow or extended release (e.g. special coating, special excipients such as insoluble polymers etc.) may be avoided or reduced.

The amlodipine fumarate may also be obtained in an amorphous form, e.g. by freeze drying a solution of amlodipine and fumaric acid in a proper solvent, e.g. in water. Such amorphous forms may be advantageous in comparison with the crystalline forms as it may be obtained in a finely powdered form with good solubility properties.

Amlodipine fumarates and particularly amlodipine hemifumarate may exist in a solvent-free form or it may be isolated as a hydrate or a solvate. The hydrates and solvates of amlodipine fumarate, especially hydrates or solvates of amlodipine hemifumarate, form another aspect of the invention.

Amlodipine fumarate may be characterised by a variety of ordinary methods such as IR spectrum, m.p., DSC curve, etc. The structure and amlodipine/fumaric acid ratio may be proven by measuring $^1$H-NMR spectrum and/or by titration methods.

Amlodipine fumarate is converted to amlodipine free base in vivo and thus it basically shares the pharmaceutical activity of amlodipine. Accordingly, the compound may be used as a suitable form of amlodipine for administration of amlodipine into a patient in need thereof. Particularly, due to its limited solubility in body fluids, amlodipine hemifumarate is the advantageous salt form of amlodipine, especially for manufacturing slow or modified release final forms, but the use thereof is not limited thereto.

Amlodipine fumarate is a useful calcium channel blocker and thus can be used to treat any cardiac condition that would be benefited by administration of a calcium channel blocker. In particular, the amlodipine fumarate can be used to treat or prevent hypertension or angina by administering an effective amount to a patient in need thereof. The specific form of angina is not particularly limited and specifically includes chronic stable angina pectoris and vasospastic angina (Prinzmetal's angina). The compound can be administered by any suitable route including orally or parenterally. The "patients" intended to be treated include human and non-human animals especially humans and non-human mammals.

The compound is usually administered as part of a pharmaceutical composition. Accordingly, a further aspect of the invention is a pharmaceutical composition for treating or preventing hypertension or angina that comprises an effective amount of amlodipine fumarate and a pharmaceutically acceptable excipient. Excipients include any inert or non-active material used in making a pharmaceutical dosage form. For example, tablet excipients include, but are not limited to, calcium phosphate, cellulose, starch or lactose. Capsules such as those made of gelatin, may contain or carry amlodipine fumarate alone or in admixture with other excipients. Liquid dosage forms are also included such as oral liquids in the form of liquors or suspensions, as well as injectable solutions. The pharmaceutical composition may be formulated for transdermal administration in the form of a patch. All of the above described pharmaceutical compositions may optionally contain one or more of each of the following excipients: carriers, diluents, colorants, flavoring agents, lubricants, solubilizing agents, disintegrants, binders and preservatives.

The pharmaceutical composition is normally provided in a unit dose. A unit dose is typically administered once or twice daily, more typically once daily. In the case of a transdermal patch, the unit dose (one patch) is generally applied at least once a month, more commonly at least once a bi-week, and typically once a week. An effective amount of the fumaric acid addition salt of amlodipine in a unit dose for treating or preventing hypertension or angina is generally within the range of 1 to 100 mg, typically 1 to 50 mg, more typically 1 to 20 mg. In solid oral dosage forms (tablets, capsules, etc.), the pharmaceutical composition typically contains about 1, 2.5, 5.0, or 10 mg of the amlodipine fumarate. For simplicity, all amounts refer to the corresponding amount of amlodipine free base provided to the composition. Specific examples of pharmaceutical compositions include those described in EP 244944 wherein amlodipine hemifumarate is used as the active ingredient.

All of the pharmaceutical compositions described above can be made by known methods and techniques. For example, the tablets can be made by dry granulation/direct compression or by a classical wet granulation method. Typically, tablets are made by blending, filling and compressing into tablets. The blending step may comprise a wet granulation or dry granulation. Similarly, capsules can be made by blending the ingredients and filling the capsule.

The following Examples illustrate the invention.

EXAMPLE 1

Amlodipine Hemifumarate 10 g of amlodipine is dissolved in 100 ml of ethanol. To this solution is added, at room temperature, 2.83 g of fumaric acid dissolved in 100 ml of hot ethanol. The

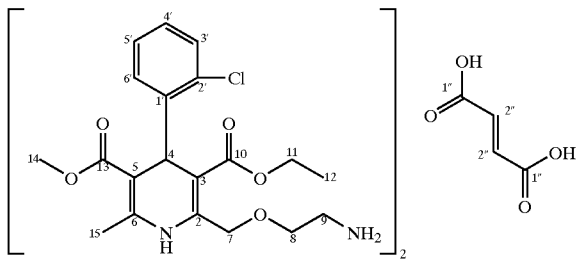

solid that is formed is filtered off and washed with 2×10 ml of ethanol. After drying in a vacuum oven at 35° C., 11 g of a white solid is obtained.

Mp: 170.5° C.–172.5° C.

$^1$H-NMR spectrum:

The $^1$H-NMR spectrum was measured at 303.2 K on a Bruker Avance-400 in deuterated acetic acid at 400 MHz.

| δ (ppm) | assignment |
|---|---|
| 1.14 | (t, 3H, $J_{11,12}$ = 7.0 Hz, H-12); |
| 2.32 | (s, 3H, H-15); |
| 3.36 | (bdd, 2H, H-9); |
| 3.59 | (s, 3H, H-14); |
| 3.90 | (bt, 2H, H-8); |

-continued

| δ (ppm) | assignment |
|---|---|
| 4.04 | (q, 2H, $J_{11,12}$ = 7.0 Hz, H-11); |
| 4.77 | (ABq, 2H, H-7); |
| 5.41 | (s, 1H, H-4); |
| 6.86 | (s, 1H, H-2"); |
| 7.05 | (dt, 1H, $J_{3',4'}$ = $J_{4',5'}$ = 7.8 Hz, $J_{4',6'}$ = 1.5 Hz, H-4'); |
| 7.15 | (dt, 1H, $J_{4',5'}$ = $J_{5',6'}$ = 7.8 Hz, $J_{3',5'}$ = 1.0 Hz, H-5'); |
| 7.23 | (dd, 1H, $J_{3',4'}$ = 7.8 Hz, $J_{3',5'}$ = 1.0 Hz, H-3'); |
| 7.41 | (dd, 1H, $J_{5',6'}$ = 7.8 Hz, $J_{4',6'}$ = 1.5 Hz, H-6'); |

$^{13}$C-NMR spectrum:

The $^{13}$C-NMR spectrum was measured at 303.2 K on a Bruker Avance-400 in deuterated acetic acid at 100.6 MHz.

| δ (ppm) | assignment |
|---|---|
| 14.53 | (C-12); |
| 19.15 | (C-15); |
| 38.29 | (C-4); |
| 40.63 | (C-9); |
| 51.54 | (C-14); |
| 61.70 | (C-11); |
| 67.72 | (C-8); |
| 68.81 | (C-7); |
| 102.93 | (C-3); |
| 104.37 | (C-5); |
| 128.04 | (C-5'); |
| 128.66 | (C-4'); |
| 130.24 | (C-3'); |
| 132.48 | (C-6'); |
| 133.26 | (C-2'); |
| 135.35 | (2 × C-2"); |
| 146.36, 146.45 | (C-2, C-6); |
| 146.85 | (C-1'); |
| 168.78 | (C-10); |
| 169.70, 169.75 | (2 × C-1", C13). |

EXAMPLE 2

Amlodipine Hemifumarate 10 g of amlodipine free base is dissolved in 75 ml of dimethylsulfoxide. To this solution is added, at room temperature, 2.84 g of fumaric acid. At room temperature, a clear solution is obtained for a few moments before a solid is formed. The solid is filtered off and washed with 2× ml of water. After drying in a vacuum oven at 50° C, 10.5 g of a white solid is obtained.

Mp: 170.8° C.–172.6° C.

EXAMPLE 3

Amlodipine Hemifumarate 5 g of fumaric acid is dissolved in a mixture of 100 ml of ethanol and 10 ml of water at 50° C. To this solution is added 5 g of amlodipine free base in portions over 10 minutes. A solid is formed approximately in 5 minutes after addition is complete. The suspension is heated until a solution is obtained and the mixture is slowly cooled to room temperature. A solid is obtained which is filtered off and washed with 2×20 ml of a ethanol/water (9/1 v:v) mixture. After drying in a vacuum oven at 40° C. for 18 hours, 3.21 g of a white solid is obtained.

Mp: 170.3° C.–172.6° C.

EXAMPLE 4

Pharmaceutical Tablet Comprising Amlodipine Hemifumarate

Composition:

| | | |
|---|---:|---:|
| ADP salt eq. to ADP base: | 5.0 mg | 10.0 mg |
| Amlodipine hemifumarate | 5.71 mg | 11.42 mg |
| Calcium hydrogen phosphate anhydrous | 63.0 mg | 126.0 mg |
| Microcrystalline cellulose | 124.1 mg | 248.1 mg |
| Sodium starch glycollate | 4.0 mg | 8.0 mg |
| Magnesium Stearate | 2.0 mg | 4.0 mg |
| Total | 198.81 mg | 397.52 mg |

Manufacturing Process:

The amlodipine hemifumarate is sieved through a 500 μm screen.

Calcium hydrogen phosphate anhydrous, microcrystalline cellulose, sodium starch glycollate and magnesium stearate are sieved through a 850 μm screen.

The amlodipine hemifumarate, calcium hydrogen phosphate anhydrous, microcrystalline cellulose and sodium starch glycollate are transferred into a free fall mixer and mixed for 15 minutes at about 25 rpm.

Magnesium stearate is added and the powder blend is mixed for another 5 minutes at about 25 rpm.

Tablets are compressed using a Korsch EK0 excenter press.

We claim:

1. Amlodipine hemifumarate having an $^1$H-NMR spectrum which includes the following δ (ppm) peak values: 1.14 (t, 3H); 2.32 (s, 3H); 3.36 (bdd, 2H); 3.59 (s, 3H); 3.90 (bt, 2H); 4.04 (q, 2H); 4.77 (ABq, 2H); 5.41 (s, 1H); 6.86 (s, 1H); 7.05 (dt, 1H); 7.15 (dt, 1H); 7.23 (dd, 1H); and 7.41 (dd, 1H); when measured at 303.2 K in deuterated acetic acid at 400 MHz; and having a $^{13}$C-NMR spectrum which includes the following δ (ppm) peak values: 14.53; 19.15; 38.29; 40.63; 51.54; 61.70; 67.72; 68.81; 102.93; 104.37; 128.04; 128.66; 130.24; 132.48; 133.26; 135.35; 146.36; 146.45; 146.85; 168.78; 169.70, and 169.75; when measured at 303.2 K in deuterated acetic acid at 100.6 MHz.

2. The amlodipine salt according to claim 1, wherein said salt is in a crystalline state.

3. A process, which comprises contacting amlodipine free base or a salt thereof with fumaric acid or its ammonium salt in the presence of a solvent to form an acid addition salt of claim 1.

4. The process according to claim 3, wherein the solvent is selected from the group consisting of water, alcohol, ketone, ester, ether, nitrile, dipolar aprotic solvent, hydrocarbon and mixtures thereof.

5. The process according to claim 4, wherein said solvent is selected from the group consisting of water, methanol, ethanol, acetone, methyl isobutyl ketone, ethylacetate, diethylether, tetrahydrofuran, acetonitrile, dimethylsulfoxide, dimethylformamide, hexane, toluene and mixtures thereof.

6. The process according to claim 5, wherein said solvent is selected from the group consisting of water, ethanol, dimethylsulfoxide, and mixtures thereof.

7. The process according to claim 3, which further comprises precipitating said acid addition salt from said solvent.

8. The process according to claim 7, wherein said precipitation is spontaneous or is induced by decreasing the temperature, decreasing the volume or adding a contrasolvent.

9. A pharmaceutical composition for use in the treatment and/or prevention of angina or hypertension comprising an effective amount of a compound according to claim 1 and a pharmaceutically acceptable excipient.

10. The pharmaceutical composition according to claim 9, wherein said composition is a unit dosage form for oral administration and said effective amount is within the range of 1–20 mg, based on the weight of the amlodipine free base.

11. The pharmaceutical composition according to claim 10, wherein said unit dosage form is a tablet or capsule form.

12. The pharmaceutical composition according to claim 11, wherein said effective amount is 2.5, 5 or 10 mg, based on the weight of the amlodipine free base.

13. A method for treating or preventing angina or hypertension which comprises administering to a patient in need thereof an effective amount of a compound according to claim 1.

* * * * *